April 29, 1952 F. L. CALUYA Plant Pat. 1,089
ROSE PLANT
Filed Jan. 23, 1951
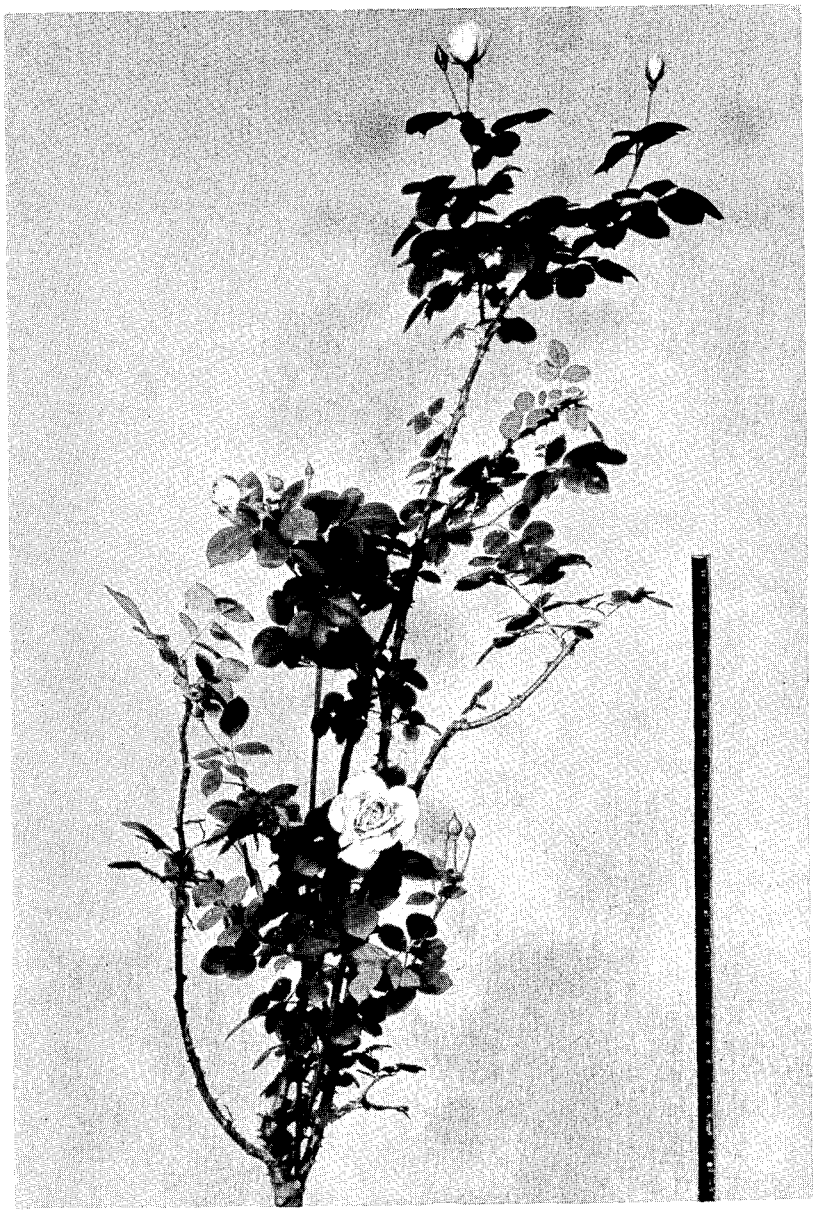
Inventor.
F. L. Caluya
By: Robb & Robb
Attorneys.

Patented Apr. 29, 1952

Plant Pat. 1,089

UNITED STATES PATENT OFFICE 1,089

ROSE PLANT

Frederick L. Caluya, Newman, Calif., assignor to Jackson & Perkins Company, Newark, N. Y., a corporation of New York Application January 23, 1951, Serial No. 207,419

1 Claim. (Cl. 47—61)

The present invention relates to a new and distinct variety of rose plant, originating as a sport of the variety "Grey Pearl" (Plant Patent No. 680) but dominantly distinguished therefrom by its climbing habit of growth. The new variety was discovered by me in a cultivated block of "Grey Pearl" plants on property owned and controlled by my employer-assignee.

The parent variety is a bush rose of the hybrid tea class, which is primarily characterized by the unique Light Mineral Gray overlaid with Light Pinkish Lilac color of its flowers and their Old Rose fragrance. Of primary importance here, however, is the fact that the parent variety has never, so far as I am aware, exhibited a climbing habit, and its growth has been that of the average strong bush rose.

The new variety has the same general form and color of flower and foliage as the parent "Grey Pearl," but sends up long, upright, climbing basal shoots from 6 to 8 feet tall, which intermittently bear flowers at the terminals of the shoots and on short axillary flowering branches, thus attaining a combination which is entirely new in the climbing rose world.

Aside from the distinguishing characteristics aforementioned, the new variety has the same characteristics that are present in the bush parent "Grey Pearl," and it is therefore unnecessary to describe the plant in detail since it conforms to the description contained in Plant Patent No. 680, excepting as to the bush habit of growth of the parent.

Asexual reproduction of the new variety by budding at Newark, New York, and at Pleasanton, California, shows that the foregoing characteristics come true to form and are established and transmitted through succeeding propagations.

The accompanying drawing shows a specimen plant of the new variety in comparison with an associated 36-inch scale or yardstick, relatively illustrating its climbing habit of growth.

I claim:

A new and distinct variety of rose plant of the climbing hybrid tea class, characterized as to novelty by its similarity to its parent "Grey Pearl" (Plant Patent No. 680), but dominantly distinguished therefrom by its climbing habit of growth and by its habit of bearing flowers at the terminals of its long, upright, climbing basal shoots and on short axillary flowering branches, substantially as shown and described herein.

FREDERICK L. CALUYA.

No references cited.